US010105699B2

(12) United States Patent
Bodner

(10) Patent No.: US 10,105,699 B2
(45) Date of Patent: Oct. 23, 2018

(54) SPLITTABLE FLUID SAMPLE COLLECTOR

(71) Applicant: Moishe Bodner, Brooklyn, NY (US)

(72) Inventor: Moishe Bodner, Brooklyn, NY (US)

( * ) Notice: Subject to any disclaimer, the term of this patent is extended or adjusted under 35 U.S.C. 154(b) by 0 days.

(21) Appl. No.: 14/932,718

(22) Filed: Nov. 4, 2015

(65) Prior Publication Data

US 2017/0120238 A1    May 4, 2017

(51) Int. Cl.
| | |
|---|---|
| *G01N 21/75* | (2006.01) |
| *G01N 31/22* | (2006.01) |
| *G01N 33/52* | (2006.01) |
| *B01L 3/00* | (2006.01) |
| *G01N 1/28* | (2006.01) |
| *A61B 10/00* | (2006.01) |

(52) U.S. Cl.
CPC ........ *B01L 3/5023* (2013.01); *A61B 10/0045* (2013.01); *A61B 10/0051* (2013.01); *G01N 1/28* (2013.01); *B01L 2200/06* (2013.01); *B01L 2300/069* (2013.01); *B01L 2300/0832* (2013.01); *B01L 2300/12* (2013.01)

(58) Field of Classification Search
CPC ........ G01N 15/06; G01N 33/00; G01N 33/48; G01N 21/75; G01N 31/22; G01N 33/52
USPC ...... 422/68.1, 411, 419, 420, 430, 559, 547, 422/549, 552, 556, 558, 560, 561; 436/63, 65, 66; 435/4, 287.6, 287.7, 435/288.1
See application file for complete search history.

(56) References Cited

U.S. PATENT DOCUMENTS

| | | | | |
|---|---|---|---|---|
| 2,133,892 | A | | 10/1938 | Gelinski |
| 4,892,525 | A | * | 1/1990 | Hermann, Jr. ........ A61M 5/002 206/365 |
| 5,501,369 | A | | 3/1996 | Tal |
| 5,910,122 | A | * | 6/1999 | D'Angelo ...................... 600/573 |
| 5,922,614 | A | * | 7/1999 | Cesarczyk ................... 436/180 |
| 6,346,086 | B1 | | 2/2002 | Maksem et al. |
| 6,372,516 | B1 | * | 4/2002 | Sun .............................. 436/518 |

(Continued)

FOREIGN PATENT DOCUMENTS

| | | |
|---|---|---|
| GB | 2460374 A | 12/2009 |
| WO | 2011106784 A1 | 9/2011 |

OTHER PUBLICATIONS

"Office Action Restriction" dated Jul. 5, 2016 in related U.S. Appl. No. 13/921,667.

(Continued)

*Primary Examiner* — Brian J. Sines
(74) *Attorney, Agent, or Firm* — Kaplan Breyer Schwarz, LLP

(57) ABSTRACT

A splittable fluid sample collector for dividing a fluid sample into two or more portions, includes at least first and second fluid collector portions detachably connected to one another, each of the fluid collector portions including a handle and an absorbent sample pad affixed to an end of the handle. Further, a fluid sampling apparatus includes the aforementioned splittable fluid sample collector, at least one container and a closure for the container. Still further, a method for splitting a fluid sample including providing the aforementioned splittable fluid sample collector, collecting a fluid sample with the absorbent sample pads of the splittable fluid sample collector and splitting the first and second fluid collector portions of the splittable fluid sample collector from one another.

28 Claims, 11 Drawing Sheets

(56) References Cited

U.S. PATENT DOCUMENTS

| | | | |
|---|---|---|---|
| 6,416,715 B1* | 7/2002 | Gambert et al. | 422/513 |
| 6,423,550 B1* | 7/2002 | Jenkins et al. | 436/518 |
| 6,634,243 B1* | 10/2003 | Wickstead et al. | 73/863.23 |
| 6,896,741 B2* | 5/2005 | Stelcher | A47L 25/005 134/6 |
| 7,618,591 B2 | 11/2009 | Slowey et al. | |
| 2001/0008614 A1* | 7/2001 | Aronowitz | 422/101 |
| 2002/0042082 A1* | 4/2002 | Nazareth et al. | 435/7.5 |
| 2006/0018800 A1* | 1/2006 | Slowey et al. | 422/102 |
| 2006/0245977 A1 | 11/2006 | Bodner | |
| 2009/0181451 A1 | 7/2009 | Slowey et al. | |
| 2010/0040506 A1* | 2/2010 | Polzius et al. | 422/58 |
| 2010/0099127 A1 | 4/2010 | Bodner | |
| 2010/0122587 A1* | 5/2010 | Sun | 73/864 |
| 2012/0067144 A1* | 3/2012 | Slowey et al. | 73/864.73 |
| 2013/0344615 A1 | 12/2013 | Bodner et al. | |
| 2014/0315221 A1 | 10/2014 | Morsey | |

OTHER PUBLICATIONS

"Non Final Office Action" dated Oct. 7, 2016 in related U.S. Appl. No. 13/921,667.
Extended European Search Report issued in counterpart European patent application No. EP16196975, dated Mar. 22, 2017.
"Examination Report" issued in counterpart Australian patent application No. 2016247235, dated May 26, 2017.
"Allowed Claims" in counterpart Australian patent application No. 2016247235, dated Dec. 12, 2017.
Eva De Kool, "Examination Report No. 2" issued in counterpart Australian patent application No. 2016247235, dated Dec. 13, 2017.

* cited by examiner

SPLITTABLE FLUID SAMPLE COLLECTOR

FIELD

The disclosure relates to fluid sampling. More particularly, the disclosure relates to a splittable fluid sample collector for a fluid sampling apparatus which collects and stores a fluid sample, the splittable fluid sample collector being splittable into two or more fluid collector portions each having an absorbent sample pad absorbed with a portion of the fluid sample.

BACKGROUND

Body fluids have long been used to diagnostically test and monitor for various biochemical and/or physiological conditions of a person's body. Typically, blood and urine samples are used to analyze and determine various conditions of the body.

More recently, oral fluids or saliva have been used to analyze and provide valuable information regarding various bodily conditions. For example, saliva may be used for diagnostically testing an individual for a variety of medical conditions or drug use including, without limitation, hepatitis, HIV, nicotine and cocaine. Clinics for oncology, neurology, infertility, allergy, orthopedic and pain typically use samples of saliva for such testing.

The use of saliva as a diagnostic test medium can be more desirable than blood because saliva is readily obtained without the use of intrusive sampling methods, such as needles and syringes. Saliva testing can also be more desirable than urine testing because saliva sampling can be easily monitored to ensure that the sample has been obtained from the person of interest.

Devices designed for sampling saliva and other fluids may use an absorbent collection pad or member to absorb a fluid specimen. Since the diagnostic test may need to be repeated to adequately identify or verify a condition, at least a second fluid sample may be required. Currently, this may require a technician to obtain a second fluid sample from the person using a second sampling device, which increases the cost, time, and inconvenience of sampling.

Accordingly, a device, apparatus, and method are needed, which reduce or eliminate the need for obtaining multiple fluid samples.

SUMMARY

Disclosed herein is a splittable fluid sample collector for dividing a fluid sample into two or more portions. The splittable fluid sample collector may comprise, in various embodiments, at least first and second fluid collector portions detachably connected to one another, each of the fluid collector portions including a handle and an absorbent sample pad affixed to an end of the handle.

Further disclosed herein is a fluid sampling apparatus. The fluid sampling apparatus may comprise, in various embodiments, a container and the above-described splittable fluid sample collector.

Further disclosed herein is a method for splitting a fluid sample comprising providing the above-described splittable fluid sample collector, collecting a fluid sample with the absorbent sample pads of the splittable fluid sample collector and splitting the first and second fluid collector portions of the splittable fluid sample collector from one another.

In some embodiments, the absorbent sample pads are arranged opposite one another.

In some embodiments, the absorbent sample pads at least partially contact one another.

In some embodiments, the handles are arranged opposite one another.

In some embodiments, the handles at least partially contact one another.

In some embodiments, the handles are detachably connected to one another with one or more frictionally engaging connecting elements.

In some embodiments, the handles are detachably connected to one another with one or more frangible welds or a frangible adhesive.

In some embodiments, the absorbent sample pads are connected to one another by one or more frangible elements.

In some embodiments, the one or more frangible elements comprise one or more uncut portions of pad material.

The same reference numerals are used in the drawings to identify the same or similar elements and structures in the various embodiments.

BRIEF DESCRIPTION OF THE DRAWINGS

FIG. 4A shows the collector prior to splitting, FIG. 4B shows the splitting of the collector, and FIG. 4C, shows the collector after being split and separated into first and second fluid collector portions.

FIG. 6A shows the collector prior to splitting, FIG. 6B shows the splitting of the collector by a technician or user, and FIG. 6C shows the collector after being split and separated into first and second fluid collector portions.

DETAILED DESCRIPTION

Figure 1:
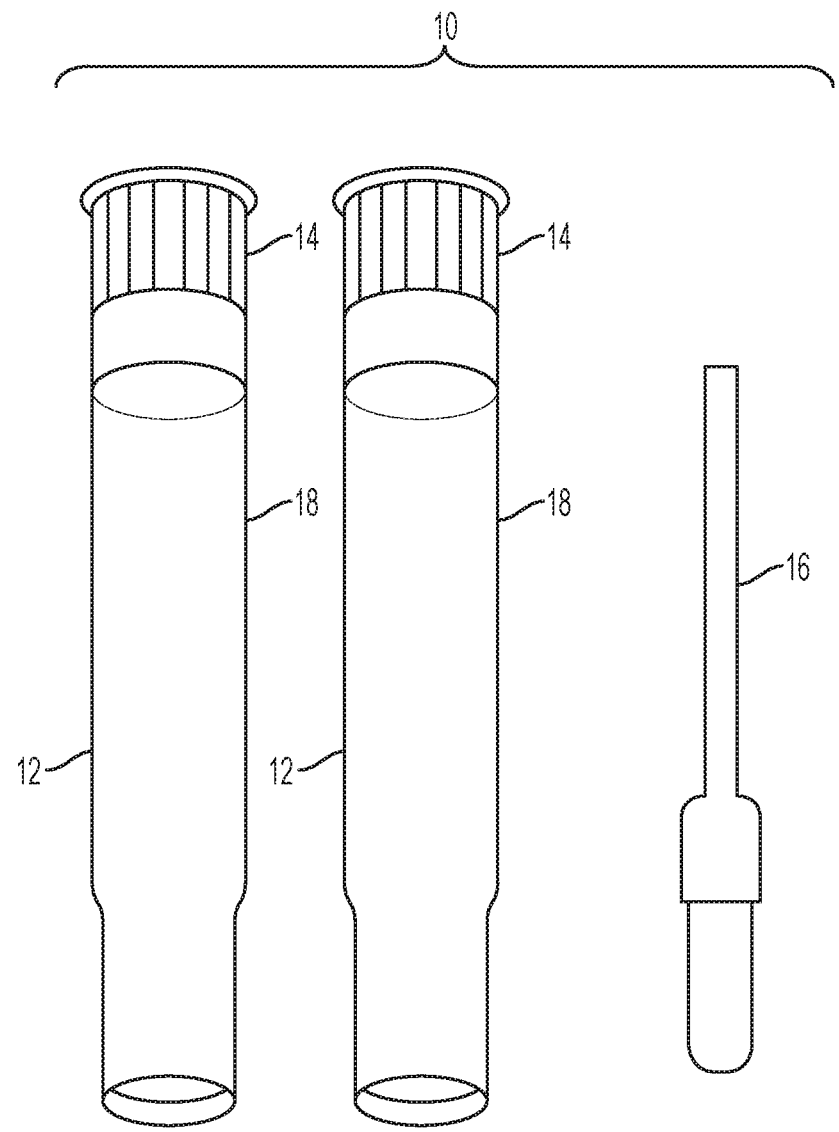
FIG. 1 is a perspective view of an embodiment of a fluid sampling apparatus of the present disclosure.

FIG. 1 depicts an embodiment of a fluid sampling apparatus 10 for collecting and storing a fluid sample, such as saliva, other body fluid, or a fluid other than a body fluid. As shown, the fluid sampling apparatus 10 may comprise one or more containers 12 each having a closure 14, and a splittable fluid sample collector 16. The splittable fluid sample collector 16 is constructed so that a technician or user can collect a single fluid sample from a person without touching the sample and then divide the fluid sample into two or more sample portions.

Figure 2:
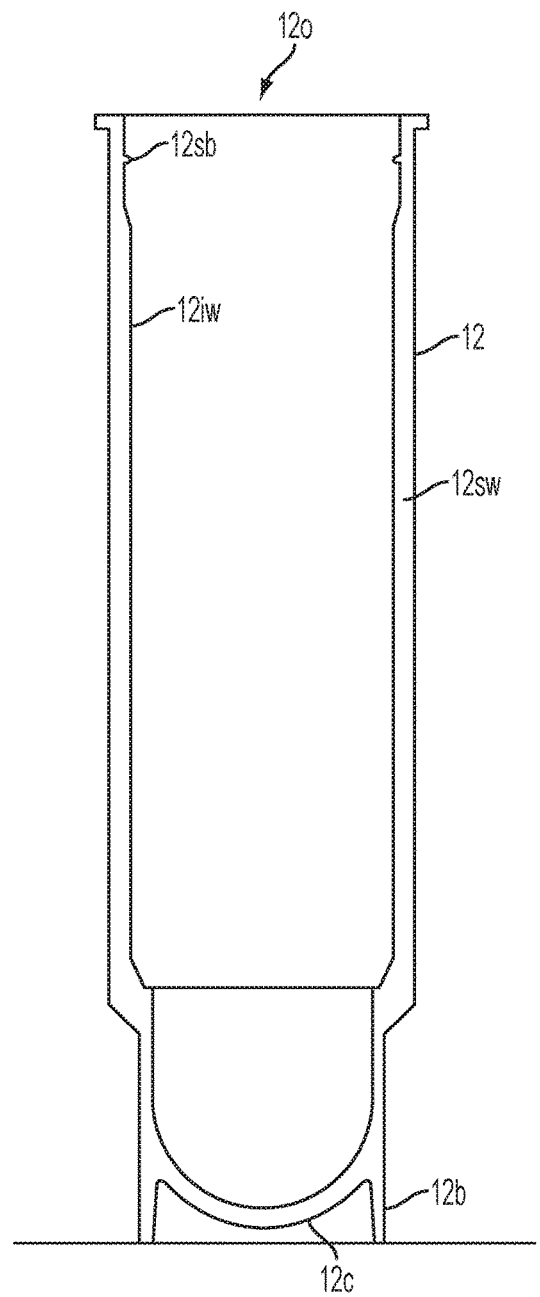
FIG. 2 is a sectional elevational view of an illustrative embodiment of a container of the fluid sampling apparatus of the present disclosure.

Referring to FIG. 2, some embodiments of the container 12 may have a tube-like configuration comprising a side wall 12sw having a closed end 12c with a rim-like base 12b and an open end 12o disposed opposite to the closed end 12c. The base 12b allows the container 12 to stand up-right on a support surface. A sealing bead 12sb may be provided on an inner side 12iw of the side wall 12sw, near its open end 12o. In some embodiments, the container 12 may contain a solution, such as a buffer solution, to maintain and/or stabilize the pH of the fluid sample.

Figure 3:
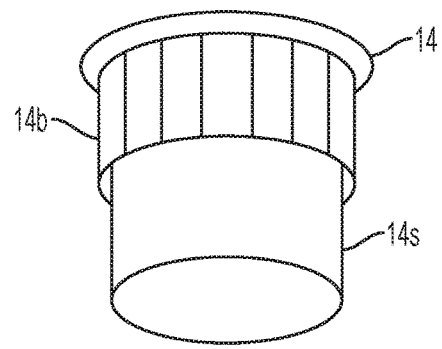
FIG. 3 is a perspective view of an illustrative embodiment of a closure of the fluid sampling apparatus of the present disclosure.

Referring to FIG. 3, some embodiments of the closure 14 may include a body 14b and a stopper member 14s axially extending from the body 14b. The closure 14 may be used for closing the open end 12o of the container 12 (FIG. 1) and may be constructed to mechanically couple to the open end 12o of the container 12 so that the stopper member 14s enters the container 12 and engages the sealing bead 12sb on the inner surface 12iw of the container side wall 12sw thereof in a hermetic manner.

Figure 4A:
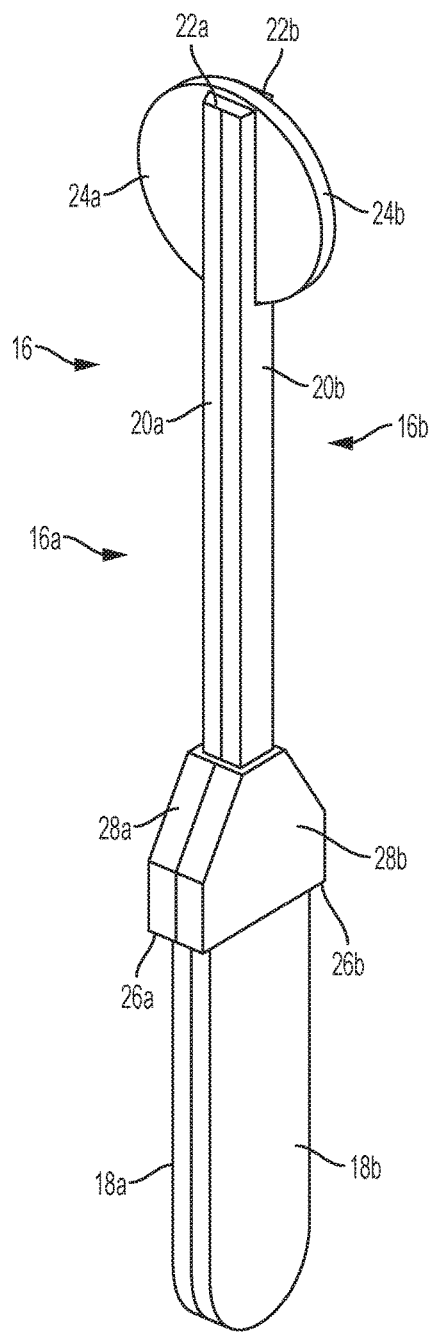
FIGS. 4A-4C are perspective views of an illustrative embodiment of a splittable fluid sample collector of the fluid sampling apparatus of the present disclosure, where
Figure 4B:
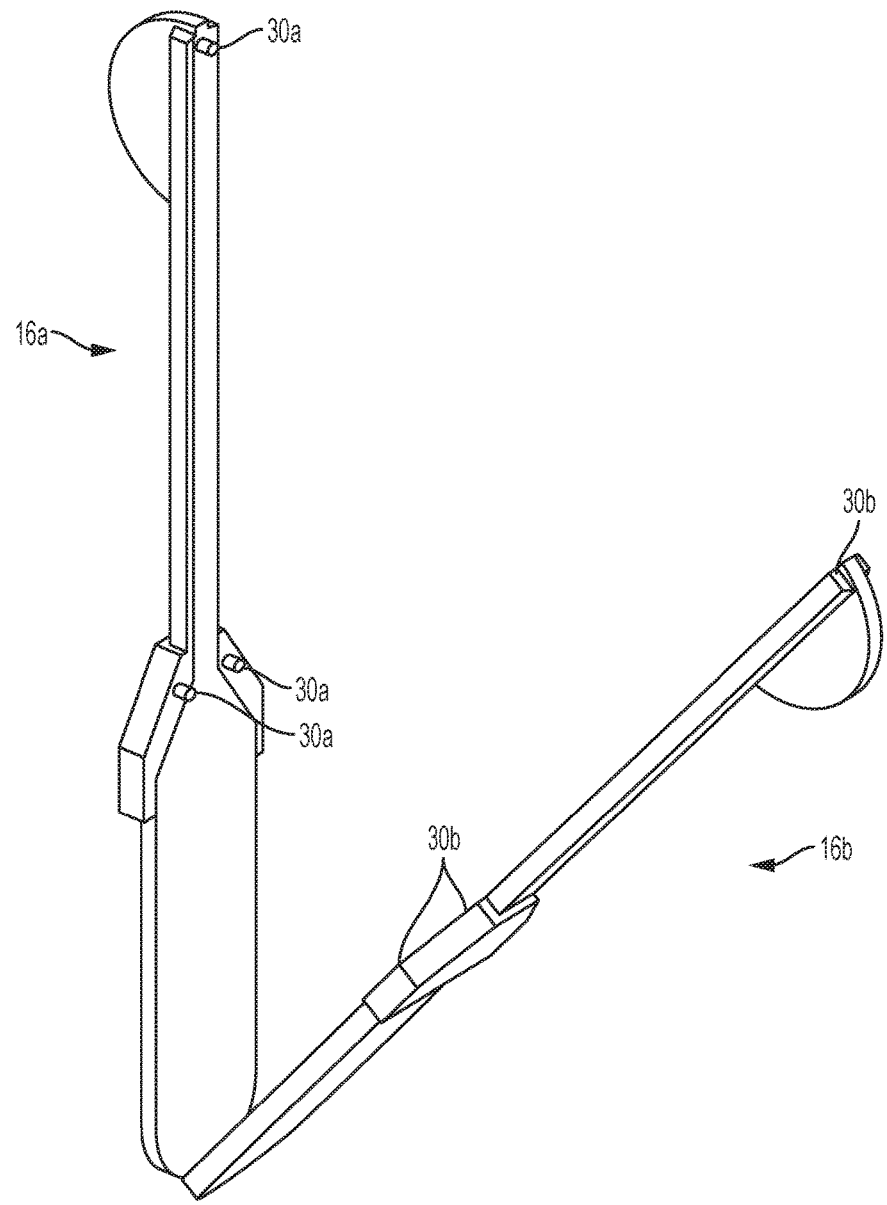
Figure 4C:
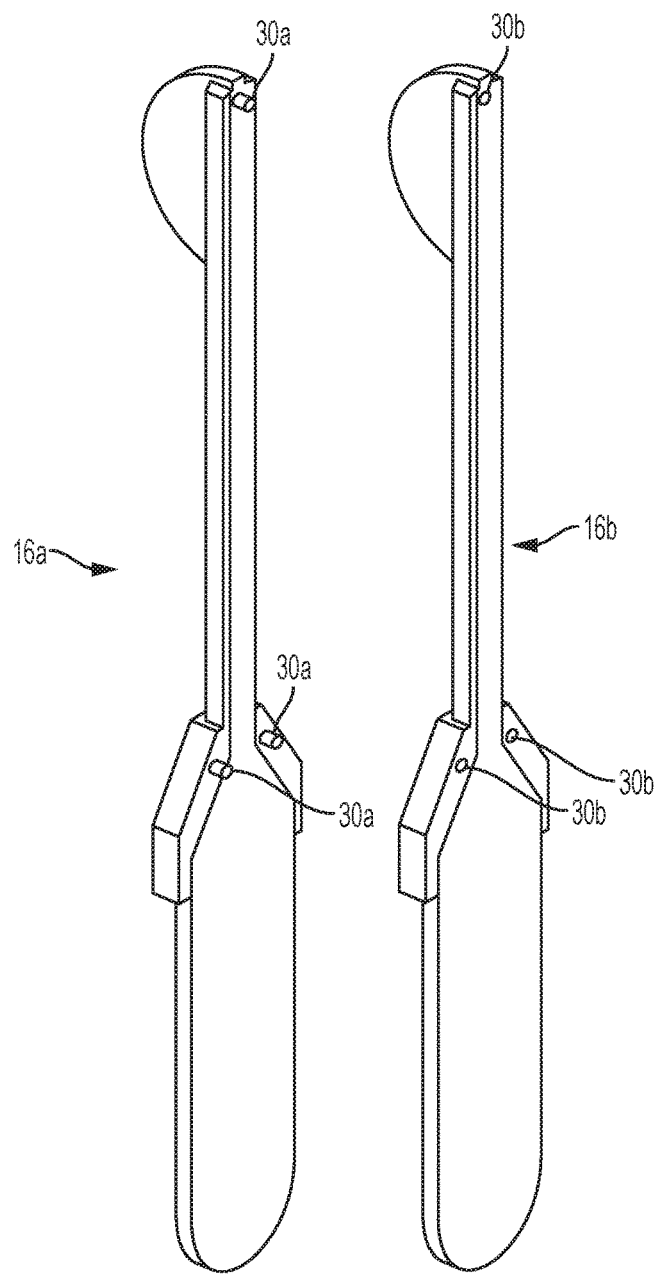

FIG. 4A-4C collectively illustrate the splittable fluid sample collector 16 according to one embodiment of the present disclosure. As shown, the splittable fluid sample collector 16 comprises first and second fluid collector portions 16a and 16b arranged opposite one another and detachably connected to one another so that the technician or user can obtain the fluid sample and then divide the fluid sample into two sample portions by splitting and separating the first and second fluid collector portions from one another. Each fluid collector portion 16a, 16b may comprise an absorbent sample pad 18a, 18b and a handle 20a, 20b. The handles 20a, 20b can be arranged opposite one another and can at least partially or fully contact one another. The absorbent sample pads 18a, 18b can be arranged opposite one another and can at least partially or fully contact one another. The absorbent sample pads, in embodiments of the fluid sample collector that comprise three or more fluid collector portions, can have one or more openings that allow the fluid sample to contact and be absorbed by the inner-most absorbent sample pads. The absorbent sample pads, in still other embodiments of the fluid sample collector, can be spaced from one another to allow the fluid sample to contact and be absorbed by the inner-most absorbent sample pads and/or the opposing inner surfaces of the pads. The handles 20a, 20b can each include a finger gripping element 24a, 24b at a free first end 22a, 22b thereof and a receptacle member 28a, 28b at an opposite second end 26a, 26b thereof, for fixedly receiving and holding an end portion 19a, 19b of the absorbent sample pad 18a, 18b. The finger gripping elements 24a, 24b allow the technician or user to manually grasp the collector 16 and/or split and separate the fluid collector portions 16a, 16b from one another. In embodiments where the fluid sample to be taken is a saliva sample, the portions of the absorbent sample pads 18a, 18b, which extend from the handles 20a, 20b, may be sized and shaped in some embodiments to be comfortably placed in a mouth of a person to be sampled to absorb and thereby collect a sample of saliva fluid therefrom for diagnostic testing. In such embodiments, the portions of the absorbent sample pads 18a, 18b extending from the handles 20a, 20b can be shaped like a conventional tongue depressor, as shown in FIGS. 4A-4C.

Figure 5:
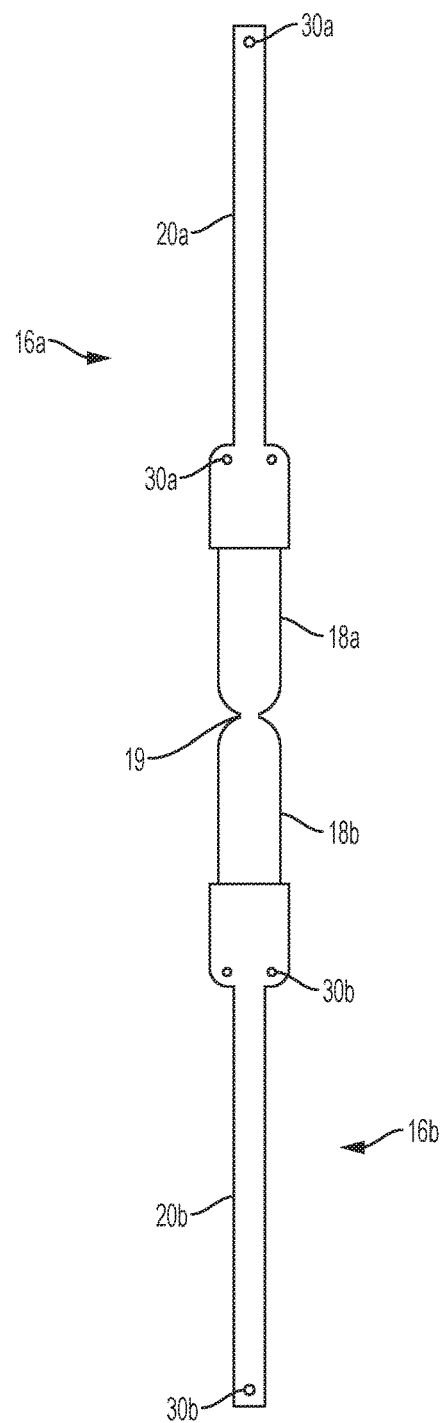
FIG. 5 is a plan view of the splittable fluid sample collector shown in FIGS. 4A-4C, illustrating a frangible element connecting absorbent sample pads of the collector prior to completion of the splitting process.

As shown in FIGS. 4B and 4C, the fluid collector portions 16a, 16b of the splittable fluid sample collector 16 can be detachably connected to one another with one or more pin-shape connecting elements 30a provided on the handle 20a of one of the fluid collector portions 16a, which frictionally engage(s) or is (are) received in one or more corresponding aperture-shape connecting elements 30b provided in the handle 20b of the other fluid collector portion 16b, when the fluid collector portions 16a, 16b are detachably connected to one another prior to splitting and separation. In other embodiments, the fluid collector portions 16a, 16b can be detachably connected to one another with one or more frangible welds formed on the handles 20a, 20b (not shown) using conventional plastic welding techniques. In still other embodiments the fluid collector portions 16a, 16b can be detachably connected to one another with a frangible adhesive applied to opposing surfaces of the handles 20a, 20b. Further, the absorbent sample pads 18a, 18b, in some embodiments of the splittable fluid sample collector 16, can also be connected to one another by an uncut portion of absorbent sample pad material 19, as illustrated in FIG. 5, which can easily be torn or broken to completely separate the fluid collector portions 16a, 16b from one another after (or before) sampling.

Figure 6A:
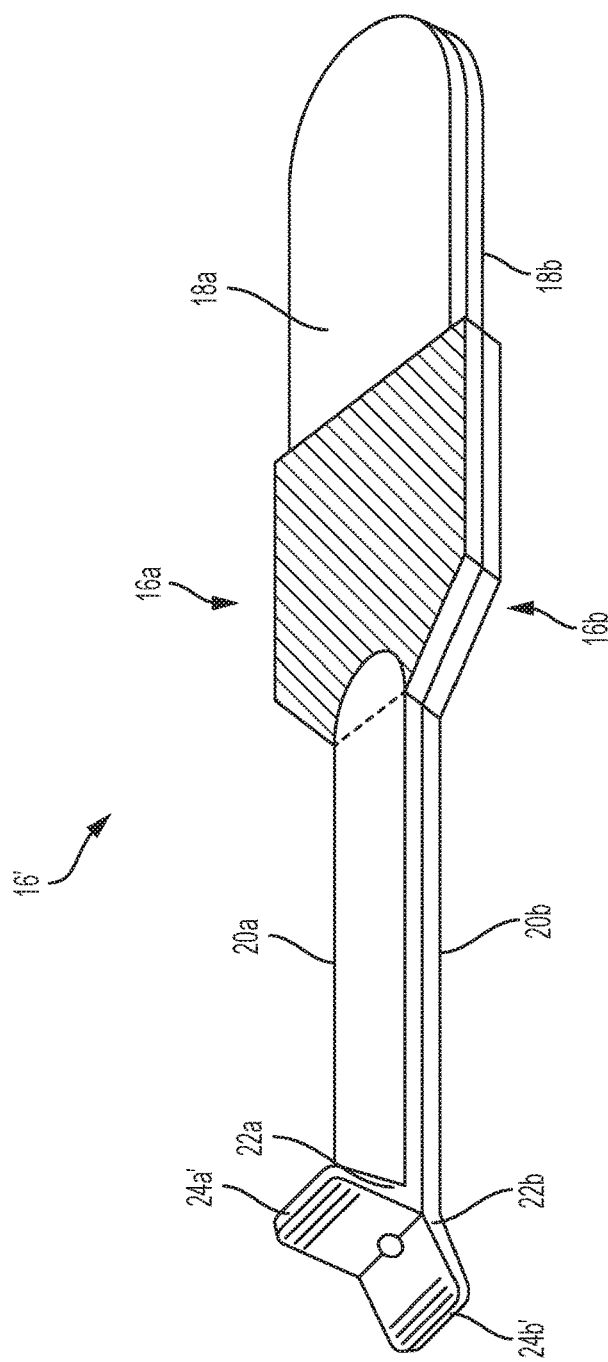
FIGS. 6A-6C are perspective views of another illustrative embodiment of the splittable fluid sample collector of the fluid sampling apparatus of the present disclosure, where
Figure 6B:
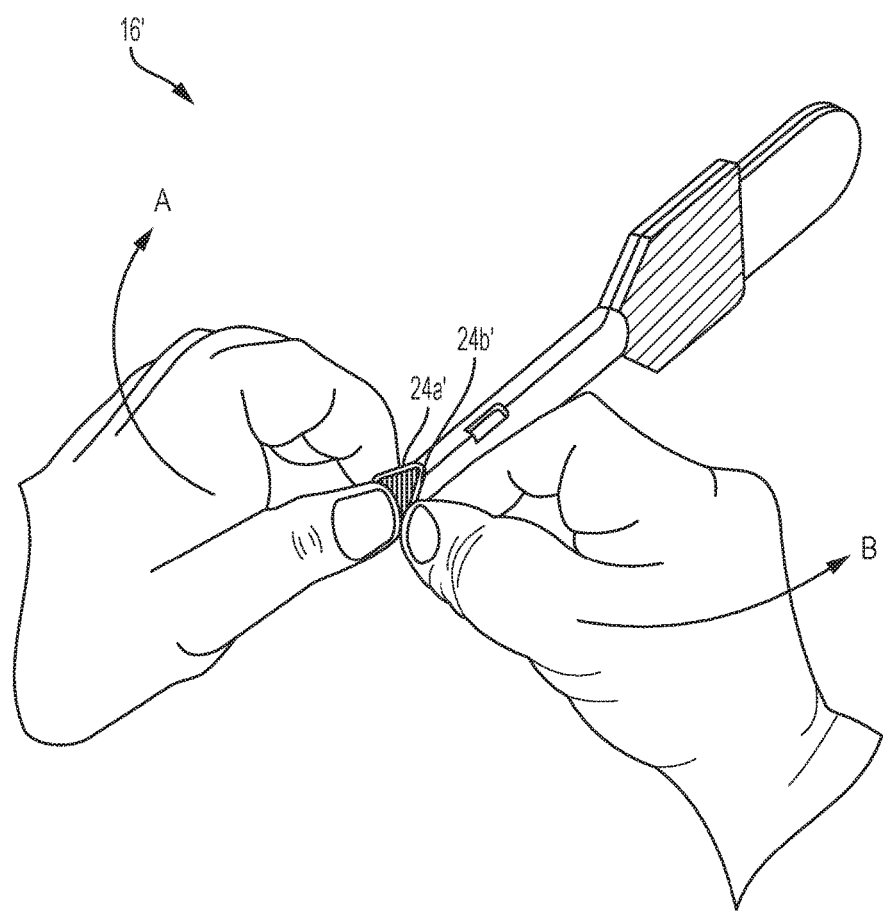
Figure 6C:
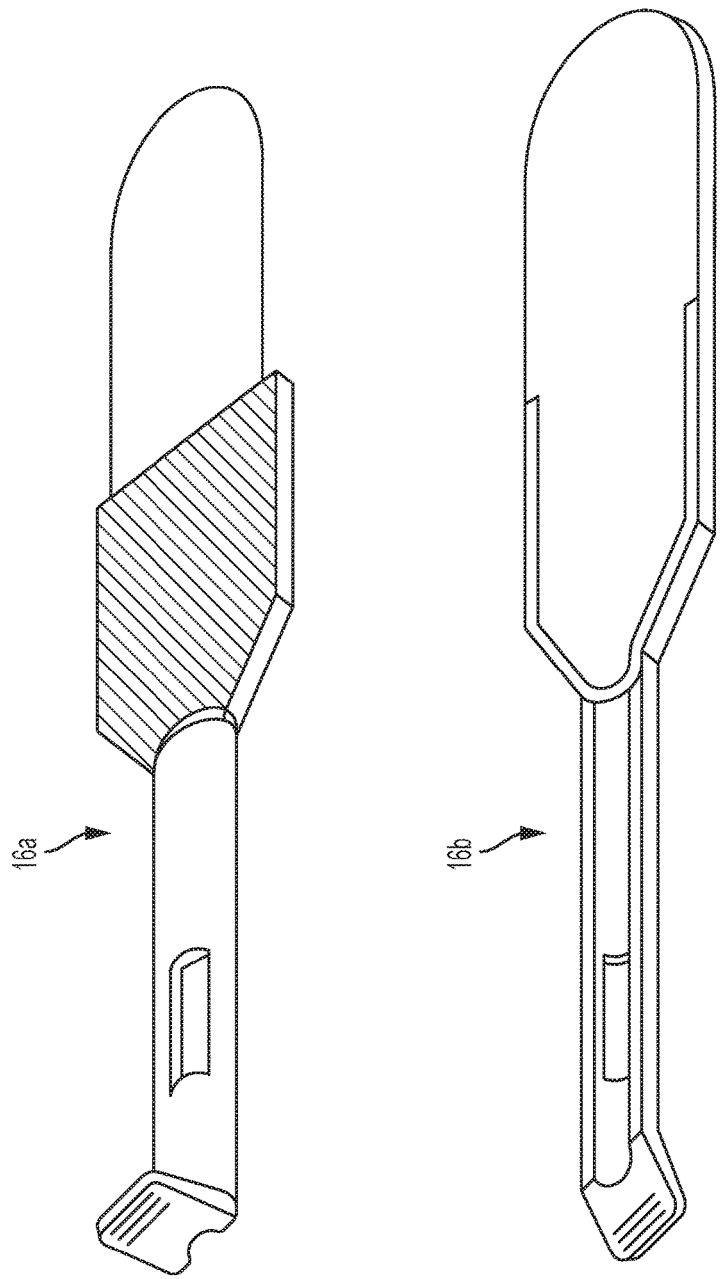

In the embodiment illustrated in FIGS. 4A-4C, the finger gripping elements 24a, 24b each have an ear-shape configuration that projects laterally from their corresponding handle 20a, 20b at the first free end 22a, 22b thereof. In another embodiment, as shown in FIGS. 6A-6C, the finger gripping elements 24a', 24b' of the splittable fluid sample collector 16' each have a flap-shape configuration that projects axially and at an angle from the free first end of 22a, 22b of their corresponding handle 20a, 20b, so that when the fluid collector portions 16a, 16b are connected to one another, the finger gripping elements 24a', 24b' diverge from one another.

The container 12, the handles 20a, 20b of the splittable fluid sample collector 16, 16' and/or the closure 14 may be formed from a thermoplastic material or any other suitable material using conventional plastic forming techniques. The absorbent sample pads 18a, 18b can comprise a piece of filter paper or any other suitable material that is capable of absorbing fluid such as saliva or any other desired fluid.

Figure 7:
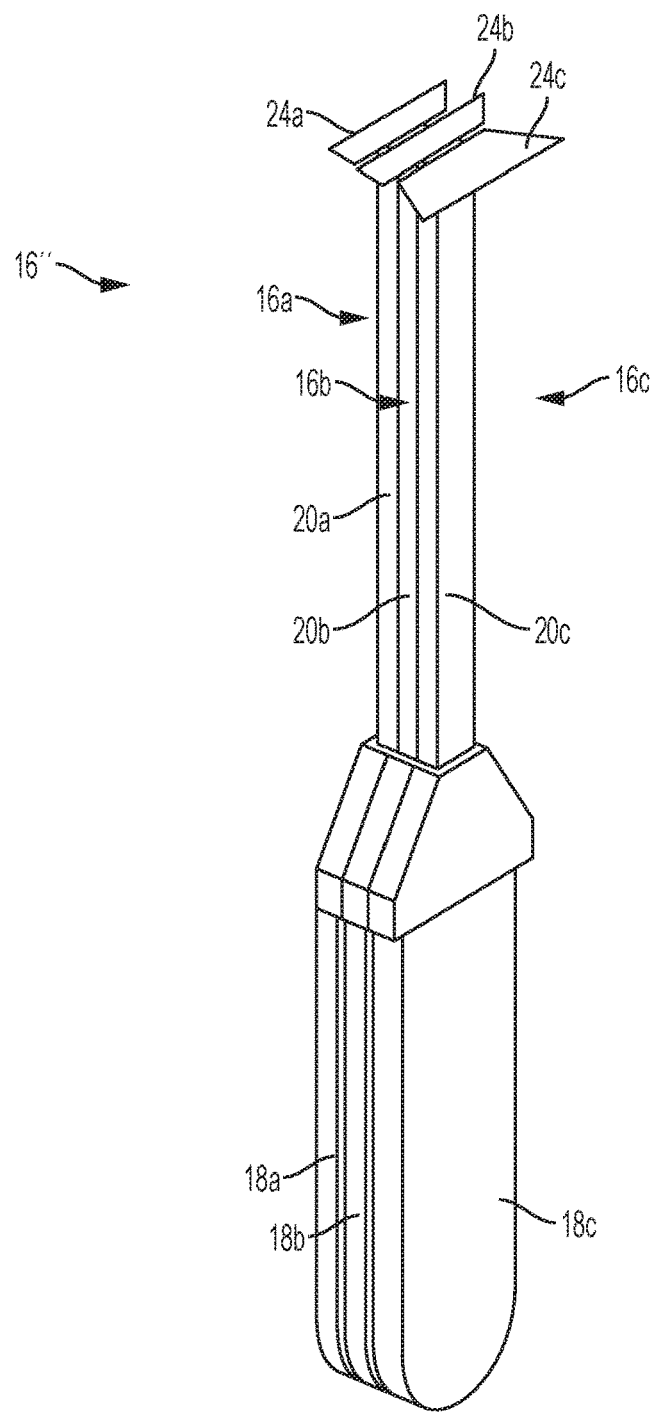
FIG. 7 is a perspective view of another illustrative embodiment of the splittable fluid sample collector of the fluid sampling apparatus of the present disclosure.

FIG. 7 illustrates another embodiment of the splittable fluid sample collector 16" according to the present disclosure. The splittable fluid sample collector 16" is similar to the splittable fluid sample collectors of FIGS. 4A-C and 6A-6C, except that it comprises three fluid collector portions 16a, 16b, 16c.

An illustrative embodiment of a fluid sampling method using the fluid sampling apparatus of the present disclosure will now be described with reference to FIGS. 1 and 6A-6C. One of ordinary skill in the art will of course appreciate that the method is also applicable to the embodiments of FIGS. 4A-4C and FIG. 7. For the purpose of illustration only, the method will be described as it pertains to obtaining a salvia sample. One of ordinary skill in the art will of course recognize that the method can also be used to obtain other types of bodily fluid samples including but not limited to blood, urine, and sweat, and non-bodily fluid samples including but not limited to well water, oil, and gas condensates. In the method, the technician or user grasps the splittable fluid sample collector 16 of FIG. 6A by the handles 20a, 20b (the fluid collector portions 16a, 16b are connected to one another) and places the absorbent sample pads 18a, 18b of the collector 16 into the mouth of a person from whom it is desired to collect the saliva fluid sample from. Once the absorbent sample pads 18a, 18b have absorbed the fluid sample, the technician or user may grasp the collector 16 by the handles 20a, 20b and remove the pads 18a, 18b from the person's mouth. If only one saliva fluid sample is desired, the technician or user can place the splittable fluid sample collector 16 with the fluid collector portions 16a, 16b connected to one another, into one of the containers 12 (pad end first) and close the container with the closure 14 and save the splittable collector 16 for future testing. If the more than one fluid sample is desired, the technician or user can split and separate the fluid collector portions 16a, 16b of the splittable fluid sample collector 16, as shown in FIG. 6B, by grasping each of the finger gripping elements 24a', 24b' with two fingers of one of the technician's or user's hand and pulling the fluid collector portions 16a, 16b apart from one another in the direction of arrows A and B to split and separate the fluid collector portions 16a, 16b from one another. Once separated from one another, as shown in FIG. 6C, the fluid collector portions 16a, 16b can each be placed into their own container 12 and the container 12 closed with a corresponding closure 14 and saved for future testing.

In other embodiments of the method, the fluid collector portions 16a, 16b of the splittable fluid sample collector 16 can be split and separated from one another prior to use in collecting a fluid sample. In such embodiments, each of the fluid collector portions 16, 16b can then be used separately to collect a fluid sample.

Although the fluid sampling apparatus and splittable fluid sample collector of the disclosure have been described in terms of illustrative embodiments, they are not limited thereto. Rather, the appended claims should be construed broadly, to comprise other variants and embodiments of the fluid sampling apparatus and splittable collector, which may be made by those skilled in the art without departing from the scope and range of equivalents of the fluid sampling apparatus and the splittable fluid sample collector elements.

What is claimed is:

1. A splittable fluid sample collector comprising at least first and second fluid collector portions, each of the fluid collector portions including a handle and an absorbent sample pad affixed to and extending from an end of the handle, the handles of the at least first and second fluid collector portions detachably connected to one another, wherein the absorbent sample pad of each of the first and second fluid collector portions includes a first planar face surface, a second planar face surface, and a peripheral edge surface extending between the first and second planar face surfaces, wherein the first and second planar face surfaces of each sample pad has a width that is greater than a width of the peripheral edge surface of the sample pad, wherein the absorbent sample pads are arranged opposite one another so that one of the first and second planar face surfaces of the absorbent sample pad of the first fluid collector portion faces one of the first and second planar face surfaces of the absorbent sample pad of the second fluid collector portion and the peripheral edge surfaces of the absorbent sample pads of the first and second fluid collector portions face a same direction, and wherein the first and second handles each includes a finger gripping element.

2. The splittable fluid sample collector according to claim 1, wherein the absorbent sample pads at least partially contact one another.

3. The splittable fluid sample collector according to claim 2, wherein the handles are arranged opposite one another.

4. The splittable fluid sample collector according to claim 1, wherein the handles at least partially contact one another.

5. The splittable fluid sample collector according to claim 1, wherein the handles at least partially contact one another.

6. The splittable fluid sample collector according to claim 1, wherein the handles are arranged opposite one another.

7. The splittable fluid sample collector according to claim 1, wherein the handles are detachably connected to one another with one or more frictionally engaging connecting elements.

8. The splittable fluid sample collector according to claim 7, wherein the absorbent sample pads are connected to one another by one or more frangible elements.

9. The splittable fluid sample collector according to claim 8, wherein the one or more frangible elements comprise one or more uncut portions of pad material.

10. The splittable fluid sample collector according to claim 1, wherein the finger gripping elements have an ear-shaped configuration or a flap-shape configuration.

11. The splittable fluid sample collector according to claim 1, wherein the handles are detachably connected to one another with one or more frangible welds or a frangible adhesive.

12. The splittable fluid sample collector according to claim 11, wherein the absorbent sample pads are connected to one another by one or more frangible elements.

13. The splittable fluid sample collector according to claim 12, wherein the one or more frangible elements comprise one or more uncut portions of pad material.

14. A fluid sampling apparatus comprising:
a container; and
a splittable fluid sample collector for dividing a fluid sample into two or more portions, the splittable fluid sample collector comprising at least first and second fluid collector portions, each of the fluid collector portions including a handle and an absorbent sample pad affixed to and extending from an end of the handle, the handles of the at least first and second fluid collector portions detachably connected to one another, wherein the absorbent sample pad of each of the first and second fluid collector portions includes a first planar face surface, a second planar face surface, and a peripheral edge surface extending between the first and second planar face surfaces, wherein the first and second planar face surfaces of each sample pad has a width that is greater than a width of the peripheral edge surface of the sample pad, wherein the absorbent sample pads are arranged opposite one another so that one of the first and second planar face surfaces of the absorbent sample pad of the first fluid collector portion faces one of the first and second planar face surfaces of the absorbent sample pad of the second fluid collector portion, and the peripheral edge surfaces of the absorbent sample pads of the first and second fluid collector portions face a same direction, and wherein the first and second handles each includes a finger gripping element.

15. The fluid sampling apparatus according to claim 14, wherein the absorbent sample pads at least partially contact one another.

16. The fluid sampling apparatus according to claim 15, wherein the handles are arranged opposite one another.

17. The fluid sampling apparatus according to claim 14, wherein the handles at least partially contact one another.

18. The fluid sampling apparatus according to claim 14, wherein the handles at least partially contact one another.

19. The fluid sampling apparatus according to claim 14, wherein the handles are arranged opposite one another.

20. The fluid sampling apparatus according to claim 14, wherein the handles are detachably connected to one another with one or more frictionally engaging connecting elements.

21. The fluid sampling apparatus according to claim 20, wherein the absorbent sample pads are connected to one another by one or more frangible elements.

22. The fluid sampling apparatus according to claim 21, wherein the one or more frangible elements comprise one or more uncut portions of pad material.

23. The fluid sampling apparatus according to claim 14, wherein the handles are detachably connected to one another with one or more frangible welds or a frangible adhesive.

24. The fluid sampling apparatus according to claim 23, wherein the absorbent sample pads are connected to one another by one or more frangible pad material elements.

25. The fluid sampling apparatus according to claim 24, wherein the one or more frangible elements comprise one or more uncut portions of pad material.

26. The fluid sampling apparatus according to claim 14, wherein the finger gripping elements have an ear-shaped configuration or a flap-shape configuration.

27. A method for splitting a fluid sample comprising:
providing a splittable fluid sample collector comprising at least first and second fluid collector portions, each of the fluid collector portions including a handle and an absorbent sample pad affixed to and extending from an end of the handle, the handles of the at least first and second fluid collector portions detachably connected to one another, the absorbent sample pad of each of the first and second fluid collector portions including a first planar face surface, a second planar face surface, and a peripheral edge surface extending between the first and second planar face surfaces, the first and second planar face surfaces of each sample pad having a width that is greater than a width of the peripheral edge surface of the sample pad, the absorbent sample pads arranged opposite one another so that one of the first and second planar face surfaces of the absorbent sample pad of the first fluid collector portion faces one of the first and second planar face surfaces of the absorbent sample pad of the second fluid collector portion and the peripheral edge surfaces of the absorbent sample pads of the first and second fluid collector portions face a same direction, and the first and second handles each including a finger gripping element;
collecting a fluid sample with the absorbent sample pads of the splittable fluid sample collector; and
grasping the finger gripping elements and splitting the first and second fluid collector portions of the splittable fluid sample collector from one another.

28. The method according to claim 27, wherein the finger gripping elements have an ear-shaped configuration or a flap-shape configuration.

* * * * *